US011486830B2

(12) United States Patent
Gabe et al.

(10) Patent No.: US 11,486,830 B2
(45) Date of Patent: Nov. 1, 2022

(54) METHOD FOR DETERMINING ULTRAVIOLET LIGHT SENSITIVITY

(71) Applicant: KAO CORPORATION, Tokyo (JP)

(72) Inventors: Yu Gabe, Bunkyo-ku (JP); Shinya Kasamatsu, Utsunomiya (JP); Osamu Osanai, Chiba (JP); Katsuya Takeda, Hiratsuka (JP); Yoko Nakajima, Kawasaki (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/958,354

(22) PCT Filed: Dec. 28, 2018

(86) PCT No.: PCT/JP2018/048519
§ 371 (c)(1),
(2) Date: Jun. 26, 2020

(87) PCT Pub. No.: WO2019/132014
PCT Pub. Date: Jul. 4, 2019

(65) Prior Publication Data
US 2020/0393380 A1 Dec. 17, 2020

(30) Foreign Application Priority Data
Dec. 28, 2017 (JP) .............................. JP2017-254004

(51) Int. Cl.
G01N 21/76 (2006.01)
G01N 21/33 (2006.01)
G01N 21/63 (2006.01)

(52) U.S. Cl.
CPC ........... *G01N 21/763* (2013.01); *G01N 21/33* (2013.01); *G01N 21/63* (2013.01)

(58) Field of Classification Search
CPC ....... G01N 21/763; G01N 21/33; G01N 21/63
USPC ........................................................ 436/172
See application file for complete search history.

(56) References Cited

U.S. PATENT DOCUMENTS

| 7,588,785 | B2 * | 9/2009 | Evans | ................ A61K 31/375 424/729 |
| 7,986,824 | B2 * | 7/2011 | Suzuki | ................ G01N 21/6458 382/133 |
| 2004/0028631 | A1 * | 2/2004 | Schwarz | ................ A61P 17/16 424/70.1 |
| 2006/0270055 | A1 | 11/2006 | Popp et al. | |
| 2008/0317856 | A1 * | 12/2008 | Beutler | ................ A61K 45/06 424/474 |
| 2013/0232752 | A1 * | 9/2013 | Warren | ................ A61B 5/0082 29/407.01 |
| 2014/0336516 | A1 * | 11/2014 | Rizzo | ................ A61B 5/7275 600/476 |
| 2016/0030564 | A1 * | 2/2016 | Loupis | ................ A61P 1/02 604/20 |
| 2019/0177688 | A1 * | 6/2019 | Lin | ................ C12N 5/0656 |

FOREIGN PATENT DOCUMENTS

| DE | 10147701 | * | 4/2003 |
| EP | 1126271 | * | 2/2000 |
| JP | 2021-4750 | A | 1/2021 |
| KR | 10-0836491 | B1 | 6/2008 |
| WO | WO 2020/204183 | A1 | 10/2020 |

OTHER PUBLICATIONS

Triglia, A. et al, Journal of Food Science 1998, 63, 512-515.*
Sauermann, G. et al, Methods in Enzymology 1999, 300, 419-428.*
Musumeci F., in Integrative Biophysics 2003, Popp F. A. et al, Eds., Springer, Dordrecht, 203-230.*
Ou-Yang, H. et al, Journal of Investigative Dermatology 2004, 122, 1020-1029.*
Zastrow, L. et al, Skin Pharmacology and Physiology 2004, 17, 219-231.*
Bennett, P. V. et al, Free Radical Biology & Medicine 2005, 39, 832-839.*
Hagens, R. et al, Skin Research and Technology 2008, 14, 112-120.*
Creath, K., SPIE 2008, 7057, paper 705708, 11 pages.*
Van Wijk, E. P. A. et al, Journal of Photochemistry and Photobiology B: Biology 2010, 98, 199-206.*
Jain, A. et al, Skin Pharmacology and Physiology 2010, 23, 266-272.*
Millington, K. R. et al., Journal of Photochemistry and Photobiology B: Biology 2012, 114, 140-146.*
Ignatov, I. et al., Advances in Physics Theories and Applications 2014, 15-33.*
Millington, K. R. et al., Journal of Photochemistry and Photobiology B: Biology 2014, 133, 27-38.*
Evelson, P. et al., Journal of Photochemistry and Photobiology B: Biology 1997, 38, 215-219.*
Benard, S. et al., SÖWF-Journal 2002, 6, 40-45.*
Torinuki, W. et al, Tohoku Journal of Experimental Medicine 1981, 135, 387-393.*
Devaraj, B. et al, Current Opinion in Solid State & Materials Science 1997, 2, 188-193.*

(Continued)

*Primary Examiner* — Arlen Soderquist
(74) *Attorney, Agent, or Firm* — Oblon, McClelland, Maier & Neustadt, L.L.P.

(57) ABSTRACT

The present invention provides a method for determining a sensitivity to ultraviolet light non-invasively and immediately. A method for determining a UV sensitivity is provided involving: a step of irradiating the skin of a test subject with ultraviolet light to determine the UV sensitivity using the amount of biophotons to be detected within a specific period after the irradiation, wherein 50% or more of the specific period overlaps a period from 1 to 3 minutes after the irradiation.

13 Claims, 1 Drawing Sheet

(56) References Cited

OTHER PUBLICATIONS

Evelson, P. et al, Journal of Photochemistry and Photobiology B: Biology 1997, 38, 2 i 5-219.*
Yasui, H. et al, Biochemical and Biophysical Research Communications 2000, 269, 131-136.*
Kim, J. et al, Journal of Health Science 2005, 51, 155-160.*
Millington, K. R. et al, Polymer Degradation and Stability 2008, 93, 640-647.*
Bertogna, E. et al, 2011 SBMO/IEEE MTT-S International Microwave and Optoelectronics Conference (IMOC 2011), 2011, 449-452.*
Petersen, A. B. et al, Skin Research and Technology 2012, 18, 405-412.*
Prasad, A. et al, Journal of Biomedical Optics 2012, 17, paper 085004, 8 pages.*
International Search Report dated Mar. 19, 2019 in PCT/JP2018/048519 filed on Dec. 28, 2018, 1 page.
Hönigsmann, H., "Erythema and pigmentation," Photodermatololgy Photoimmunology & Photomedicine, vol. 18, 2002, pp. 75-81.
Ichihashi, M. et al., "UV-induced skin damage," Toxicology, vol. 189, 2003, pp. 21-39.
Fujita, H. et al., "A simple and non-invasive visualization for assessment of carbonylated protein in the stratum corneum," Skin Research and Technology, 2007, vol. 13, pp. 84-90.
Hata, T. R. et al., "Non-Invasive Raman Spectroscopic Detection of Carotenoids in Human Skin," The Journal of Investigative Dermatology, vol. 115, No. 3, 2000, pp. 441-448.
Ou-Yang, H. et al., "Dermal contributions to UVA-induced oxidative stress in skin," Photodermatology, Photoimmunology & Photomedicine, vol. 25, 2009, pp. 65-70.
Rohr, M. et al., "Influence of Repetitive UVA Stimulation on Skin Protection Capacity and Antioxidant Efficacy," Skin Pharmacology and Physiology, vol. 24, 2011, pp. 300-304.
Extended European Search Report (EESR) dated Jul. 27, 2021 for European Patent Application No. 18895200.6.
Dreher F., et al., "Topical melatonin in combination with vitamins E and C protects skin from ultraviolet-induced erythema: a human study in vivo", The British Journal of Dermatology, Aug. 1, 1998, 139(2):332-339.

* cited by examiner

METHOD FOR DETERMINING ULTRAVIOLET LIGHT SENSITIVITY

FIELD OF THE INVENTION

The present invention relates to a method for determining a UV sensitivity in which the UV sensitivity of human skin is determined and a method for evaluating or selecting a UV sensitivity-reducing agent.

BACKGROUND OF THE INVENTION

Skin is variously damaged due to exposure to sunlight. In particular, it was known that reactive oxygen species (ROS) generated in the skin by light in the UV region (290 to 400 nm) and biological oxides generated by the reaction with the ROS have adverse effects on the skin as oxidative stress and are deeply involved in the formation of erythema and hyperpigmentation caused by short-term exposure and further photoaging and carcinogenesis caused by long-term exposure (Non Patent Literatures 1 and 2).

As a technique for protecting the skin from such troubles caused by ultraviolet light, there is a method for preventing oxidative stress by applying a sunscreen agent, an antioxidant, or the like to the skin to suppress the production of ROS and biological oxides due to UV irradiation.

Meanwhile, living organisms have countermeasures such as a reactive oxygen species-eliminating system and in-vivo antioxidants against oxidative stress caused by external stimulation such as UV irradiation. However, there are individual differences in these countermeasures depending on the age, genetic factors, lifestyle habits, eating habits, and the like, and the necessity of preventive care against ultraviolet light differs in each individual. Therefore, in order to carry out effective preventive care against ultraviolet light, it is necessary to accurately evaluate the oxidative stress exerted on the skin by UV irradiation or the like and the antioxidant power in the skin.

As a method for evaluating the oxidative stress in human skin, there is a method using biopsy skin, but the method has not been widely used due to its invasiveness. Although the evaluation of oxidized proteins by stratum corneum tape stripping is minimally invasive, the evaluation is limited to only the stratum corneum and does not necessarily reflect the internal state of the skin (Non Patent Literature 3). As a non-invasive evaluation method, there is a report on carotenoid measurement in the skin by Raman spectroscopy, but this is the evaluation of a single antioxidant and does not necessarily reflect the response of the whole skin (Non Patent Literature 4).

Further, as a method for directly evaluating the sensitivity to oxidative stress due to UV irradiation, the minimum UV radiation to form erythema (MED; Minimal Erythema Dose) 24 hours after UV irradiation can be measured to be used as an index of the likelihood of erythema due to ultraviolet light. However, the erythema formation 24 hours after the UV irradiation needs to be determined, and thus it is not a simple method.

Under such circumstances, a technique for detecting weak bioluminescence (biophotons) is gaining attention as a technique capable of non-invasively evaluating the oxidation state of living organisms. Biophotons are exceptionally weak spontaneous luminescence emitted by living organisms with life activities. As the origin, singlet oxygen and excited carbonyl compounds are inferred, and it is considered that the luminescence is caused by the oxidation reaction of living organisms.

Biophotons are observed in various organisms such as plants, microorganisms, and animals. In human skin, biophotons are measured particularly after irradiation with ultraviolet A (UVA). It was reported that the luminescence intensity varies due to the difference in skin color (Non Patent Literature 5), and that the luminescence is reduced by applying an antioxidant cream (Non Patent Literature 6).

However, the evaluations are made based on the integrated values in several minutes immediately after UVA irradiation in these reports, and the response of oxidative stress, which changes every moment, is not evaluated in detail over time. Further, there are no reports showing the behavior of biophotons.

(Non Patent Literature 1) Photodermatol. Photoimmunol. Photomed. 18, 75-81 (2002)
(Non Patent Literature 2) Toxicology 189, 21-39 (2003)
(Non Patent Literature 3) Skin Res. Technol. 13, 84-90 (2007)
(Non Patent Literature 4) J. Invest. Dermatol. 115, 441- (2000)
(Non Patent Literature 5) Photodermatol. Photoimmunol. Photomed. 25, 65-70 (2009)
(Non Patent Literature 6) Skin Pharmacol. Physiol. 24, 300-4 (2011)

SUMMARY OF THE INVENTION

The present invention relates to 1) and 2) below.

1) A method for determining a UV sensitivity, comprising a step of irradiating the skin of a test subject with ultraviolet light to determine the UV sensitivity using the amount of biophotons to be detected within a specific period after the irradiation, wherein 50% or more of the specific period overlaps a period from 1 to 3 minutes after the irradiation.

2) A method for evaluating or searching for a UV sensitivity-reducing agent, comprising: a step of administering a test substance to a subject or bringing the test substance into contact with the subject; and a step of irradiating the skin or skin cells of the subject with ultraviolet light to evaluate the test substance using the amount of biophotons to be detected within a specific period after the irradiation, wherein 50% or more of the specific period overlaps a period from 1 to 3 minutes after the irradiation.

DETAILED DESCRIPTION OF THE INVENTION

Figure 1:
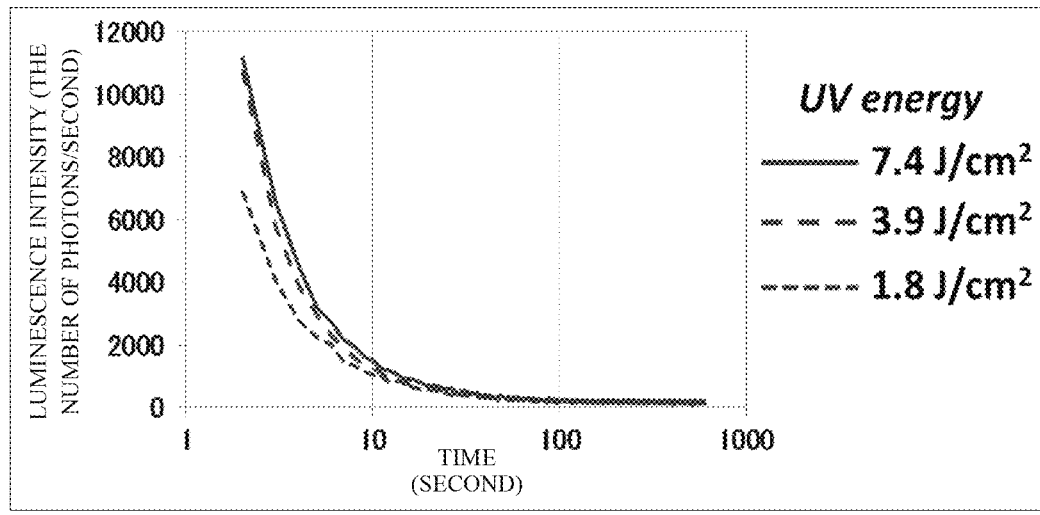
FIG. 1 is a graph showing the transition of the amount of biophotons after UV irradiation.

The present invention relates to providing a method for determining a sensitivity to ultraviolet light non-invasively and immediately, and a method for evaluating or searching for a UV sensitivity-reducing agent.

As a result of studies on a method which enables evaluation of skin damage caused by ultraviolet light at an early stage, the inventors found that biophotons to be detected within a specific time after human skin is irradiated with ultraviolet light are deeply involved in erythema formation to be developed on the next day, and the sensitivity to ultraviolet light can be evaluated, or a material which reduces the UV sensitivity can be evaluated or searched for, using the amount of the biophotons as an index.

According to the present invention, the sensitivity to ultraviolet light can be determined non-invasively and immediately, which can be used for countermeasures for preventing erythema formation due to ultraviolet light in advance, specifically, countermeasures such as physical protection against ultraviolet light and application of a UV protection skin external preparation such as a sunscreen. Also, according to the present invention, a UV sensitivity-reducing agent can be evaluated or searched for easily and efficiently.

In the method for determining a UV sensitivity of the present invention, the skin of a test subject is irradiated with ultraviolet light, and the amount of biophotons to be detected within a specific period after the irradiation is used as an index.

Further, in the method for evaluating or searching for a UV sensitivity-reducing agent of the present invention, the amount of the biophotons to be detected within a specific period after the irradiation in the case of administering a test substance to the skin or skin cells of a subject or bringing the test substance into contact with the skin or skin cells of the subject and irradiating the skin or skin cells of the subject with ultraviolet light is used as an index.

In the methods of the present invention, the ultraviolet light for irradiation is not specifically limited, as long as it is light rays having a wavelength in the ultraviolet region. Specific examples thereof include UV-B radiation having a wavelength of from 285 to 320 nm or UV-A radiation having a wavelength of from 320 to 400 nm. In the present invention, mixed ultraviolet light of A radiation and B radiation is preferable, with a ratio of the light intensity (A radiation/B radiation) of preferably from 6 to 20, more preferably from 7 to 15, further preferably from 8 to 12.

The intensity of the ultraviolet light for irradiation is not specifically limited but is preferably 10 $mW/cm^2$ or more, more preferably 20 $mW/cm^2$ or more, more preferably 30 $mW/cm^2$ or more, and preferably 200 $mW/cm^2$ or less, more preferably 170 $mW/cm^2$ or less, more preferably 150 $mW/cm^2$ or less, for example. Further, the intensity is preferably from 10 to 200 $mW/cm^2$, more preferably from 20 to 170 $mW/cm^2$, more preferably from 30 to 150 $mW/cm^2$. In the present invention, the intensity of the ultraviolet light means the intensity of ultraviolet light in the wavelength region combining UV-B radiation and UV-A radiation (285 to 400 nm).

The intensity of the ultraviolet light can be measured using a commercially available measuring instrument, and examples thereof include Solarmeter Model 5.0 (UVA+B) (Solartech Inc.) and a multipurpose spectroradiometer MSR-7000N (Opto Research Corporation).

Further, the irradiation time differs depending on the intensity of ultraviolet light for irradiation but is, for example, from 5 to 300 seconds, preferably from 5 to 240 seconds, further preferably from 5 to 200 seconds.

The UV irradiation dose (irradiation energy) determined depending on the intensity of the ultraviolet light for irradiation and the irradiation time is preferably from 300 to 8000 $mJ/cm^2$, more preferably from 500 to 7000 $mJ/cm^2$, further preferably from 600 to 6000 $mJ/cm^2$.

The UV irradiation device for irradiation with ultraviolet light is not specifically limited, as long as it is provided with a light source capable of emitting light in the aforementioned wavelength range. Examples of the light source include low-pressure mercury lamps, high-pressure mercury lamps, ultrahigh-pressure mercury lamps, xenon lamps, metal halide lamps, wood lamps, and fluorescent inspection lamps. Xenon lamps are preferable.

The irradiation wavelength is adjusted by combining a filter capable of selecting light having a wavelength in the UV region with such a light source, as required.

The skin site of the test subject to be irradiated with UV is not specifically limited, as long as it is a site which can be subjected to ultraviolet irradiation and biophoton measurement. However, the UV sensitivity of sites which are likely to be exposed to daily UV radiation may possibly vary due to the influence of daily UV irradiation, thereby causing unevenness in measured values in the methods of the present invention. Therefore, sites which are less likely to receive daily UV radiation are preferable. Specifically, examples thereof include the skin in the inner forearms, the upper inner arms, the back, the buttocks, and the abdomen. The inner forearms, the upper inner arms, the back, and the buttocks are preferable, and the inner forearms or the abdomen are more preferable.

Further, examples of the subject in the UV sensitivity-evaluating method or the selection method of the present invention include cultured epidermal cells, a 3D skin model, and a cultured skin tissue other than a human (test subject). The UV irradiation is performed on the aforementioned skin sites of the test subject, or the cells or tissue (skin) in the cultured epidermal cells or the skin culture tissue. Examples of the cultured epidermal cells preferably include epidermal keratinocytes (keratinocytes). Commercially available products such as EpiDerm™ (available from MatTek Corporation), EpiSkin (available from Skinethic Laboratories), RHE (available from Skinethic Laboratories), and Labcyte EPI-MODEL (available from Japan Tissue Engineering Co., Ltd.) can be used as three-dimensionally cultured skin cells.

As shown in Test Example 1 below, biophotons generated when irradiating the skin with UV show the maximum luminescence intensity immediately after the UV irradiation, and thereafter the luminescence decreases with time. The present invention has revealed that the luminescence intensity mainly within a period of from 1 to 3 minutes after the irradiation correlates with erythema formation observed 24 hours after the UV irradiation (Test Examples 2 and 3).

Therefore, in the method for determining a UV sensitivity or the method for evaluating or searching for a UV sensitivity-reducing agent of the present invention, a period 50% or more of which overlaps a period of from 1 to 3 minutes after the UV irradiation is referred to as a specific period, and the amount of biophotons within the specific period is used for determination or evaluation.

The specific period is set as a period 50% or more of which overlaps a period of from 1 to 3 minutes after the irradiation, but the period which overlaps the period of from 1 to 3 minutes after the irradiation is preferably 70% or more, more preferably 80% or more, more preferably 90% or more, and it is more preferable that 100% of the period overlaps the period of from 1 to 3 minutes after the irradiation.

Here, the phrase that a specific period overlaps a period of from 1 to 3 minutes after the irradiation means that the two periods have a certain period in common, and the phrase that a period 50% or more of which overlaps the period means that 50% or more of the specific period overlaps the period of from 1 to 3 minutes after the irradiation.

Further, since the amount of biophotons is large at the initial period immediately after the UV irradiation and significantly affects the determination or the evaluation of the present invention, the specific period of the present invention is preferably set so as not to overlap the initial period immediately after the UV irradiation. Specifically, it is preferably set so as not to overlap the initial period of 15 seconds, preferably 30 seconds, more preferably 45 seconds after the completion of the irradiation.

For measuring an effective amount of biophotons, the length of the specific period is preferably from 30 seconds to 3 minutes, more preferably from 40 seconds to 2 minutes, more preferably from 50 seconds to 1 minute and 30 seconds, more preferably 1 minute.

More suitable examples of the specific period include 1 minute from 1 to 2 minutes after the irradiation, 1 minute from 2 to 3 minutes after the irradiation, and 2 minutes from 1 to 3 minutes after the irradiation.

Biophotons are detected with an optical detector provided with a detection unit capable of detecting very weak biophotons such as high-sensitivity and low-noise CCD. As such an optical detector, a weak luminescence intensity detector (CLA-IDFsk, available from Tohoku Electronic Industrial CO., Ltd.) can be used, for example. The wavelength of the radiation light to be detected differs depending on the photomultiplier tube of the detector, but from 300- to 850-nm biophotons are detected in the aforementioned device. Further, the biophotons are preferably measured in a space shielded from light as much as possible, such as a dark room, for suppressing the influence of light derived from the measurement environment as much as possible.

That is, it is preferable to irradiate a site to be measured with ultraviolet light using the aforementioned UV irradiation device in a dark room and then to measure biophotons emitted from the UV-irradiated site with the weak luminescence intensity detector. Further, the UV radiation unit in the UV irradiation device and the detection unit in the weak luminescence intensity detector may be separately provided. However, the UV radiation unit (specifically, fibers for light irradiation extending from the UV irradiation device) is preferably integrated with the detection unit to form a structure capable of changing the device to be used by switching the optical path, since the UV irradiation and the detection of biophotons can be performed without replacing the device.

For the biophotons generated by the UV irradiation, the luminescence intensity when stable (referred to also as "stationary biophotons") is measured in advance before the UV irradiation, and subsequently the luminescence intensity within the specific period after the UV irradiation (referred to also as "biophotons after the irradiation") is measured. Thus, a luminescence increment (referred to also as "response biophotons") can be calculated by subtracting the luminescence intensity when stable from the latter value.

As described above, the degree of erythema observed 24 hours after the UV irradiation positively correlates with the amount of biophotons to be detected within the period of from 1 to 3 minutes after the UV irradiation. Accordingly, the amount of the biophotons can be utilized as an index for determining a sensitivity to ultraviolet light or for evaluating or searching for a UV sensitivity-reducing agent. Here, the "sensitivity to ultraviolet light" refers to the degree of inflammatory reactions such as erythema to be induced by ultraviolet light indicated by the intensity or the duration of the inflammatory reactions, and the degree of the inflammatory reactions means the sensitivity to ultraviolet light. Further, "reducing the UV sensitivity" means to mitigate or suppress the sensitivity to ultraviolet light so as to suppress the development of the inflammatory reactions such as erythema to be induced by ultraviolet light.

In the method for determining a UV sensitivity of the present invention, the amount of biophotons to be detected within a certain period after the UV irradiation in the present invention is measured for each age or age range or sex in advance to acquire basic data, and then a deviation value in the age (age range) or the sex of the test subject is calculated from the average and the standard deviation calculated from the basic data, so that the deviation value can be used as an index for determining the sensitivity to ultraviolet light, for example.

Alternatively, with respect to an index for determining the sensitivity to ultraviolet light such as high sensitivity (the skin is likely to be red), slightly high sensitivity (the skin is slightly likely to be red), standard, slightly low sensitivity (the skin is slightly less likely to be red), and low sensitivity (the skin is less likely to be red), suitable evaluation criteria for associating the index with a deviation range are prepared, and the sensitivity to ultraviolet light of the test subject can be determined from the deviation value of the test subject based on the criteria.

The method for determining a UV sensitivity as described above is capable of making a determination in a very short time as compared with conventional MED measurement, and it imposes less burden to the test subject. The information relating to the UV sensitivity obtained by the determination method of the present invention can be used for physical protection measures against ultraviolet light and measures against ultraviolet light by application of a UV protection skin external preparation such as a sunscreen, as an index for selecting a product when purchasing the UV protection skin external preparation or recommending a product in recommended sales of the UV protection skin external preparation.

The method for determining a UV sensitivity of the present invention is one of so-called methods for collecting various data from a human body by, for example, measuring the structure or function of each organ of the human body and is used for the aforementioned purpose. That is, the determination method of the present invention is not used for determining the physical conditions or mental conditions such as human pathologies and health conditions for the purpose of medical care. In such a meaning, the method for determining a UV sensitivity of the present invention can be expressed also as a method for measuring the UV sensitivity or a method for inspecting the UV sensitivity.

The evaluation or search of the UV sensitivity-reducing agent of the present invention comprises a step of administering a test substance to a subject or bringing the test substance into contact with the subject. The skin or skin cells of the subject are irradiated with ultraviolet light, and the test substance is evaluated using the amount of biophotons to be detected within a specific period after the irradiation.

Here, the test substance to be administered is not specifically limited and may be a substance naturally present or a substance artificially synthesized by a chemical or biological method or may be a compound, a composition, or a mixture. However, the test substance is preferably a known substance ensured to be safe such as substances or compositions used as pharmaceutical products, cosmetics, and raw materials thereof. In the case where the test substance is a composition such as pharmaceutical products and cosmetics, UV protection materials such as ultraviolet absorbers and UV scattering agents contained in the composition may possibly affect the amount of the biophotons to be detected, because of the physical protection against the ultraviolet light to irradiate the skin or skin cells of the subject in the UV irradiation of this evaluation or search method. Accordingly, in the case where the test substance in this evaluation or search method is a composition, the composition is preferably free from UV protection materials such as ultraviolet absorbers and UV scattering agents. Alternatively, in the case of evaluating a composition comprising a UV protection material as the test substance in this evaluation or search method, it is preferable to perform a treatment for removing the composition from the skin or skin cells of the subject before the biophoton measurement or before the UV irradiation.

The administration form of the test substance may be either one of oral and parenteral administration forms but is preferably in the form of parenteral administration. Specifically, the test substance is preferably applied to the skin in various forms such as ointments, creams, milky lotions, lotions, gels, aerosols, patches, tapes, and sprays.

Further, the number of times of administering the test substance to the subject or bringing the test substance into contact with the subject is not specifically limited. Further, the administration or contact may be performed once simultaneously with or immediately before the UV irradiation, but it is preferable that a specific administration or contact period is provided before the UV irradiation, and administration or contact is performed once or multiple times within the period at a specific administration or contact frequency. In the case where the subject is a human, the administration period is preferably one day or more, more preferably one week or more, further preferably 4 weeks or more. Further, the administration period is preferably 6 months or less, more preferably 3 months or less, further preferably 2 months or less. The administration frequency is preferably once or more, more preferably once to 5 times, further preferably once to 3 times, further preferably twice, per day.

In the case of using cultured epidermal cells, a 3D skin model, a cultured skin tissue or the like as the subject, the contact period is preferably 1 hour or more, more preferably 6 hours or more, further preferably 24 hours or more. Further, the contact period is preferably 72 hours or less, more preferably 36 hours or less, further preferably 48 hours or less. The contact frequency is preferably once or more, more preferably once to 4 times, further preferably once or twice, during the contact period.

Then, the biophotons detected within the specific period after the UV irradiation are measured, and a test substance which reduces the amount of biophotons is evaluated to be a UV sensitivity-reducing agent.

The test substance which reduces the amount of biophotons can be identified, for example, by comparing the amounts of biophotons measured when administering test substances at different concentrations. More specifically, the amounts of biophotons are compared, for example, between a higher-concentration test substance-administered group and a lower-concentration test substance-administered group; between a test substance-administered group and a placebo-administered group; between a test substance-administered group and a non-administered group; or between before and after administration of each test substance. In the case where the amount of the biophotons is reduced by administering a test substance or administering a higher-concentration test substance, the test substance can be identified to be a substance which reduces the amount of biophotons.

For example, in the case where a reduction tendency is recognized in the amount of biophotons in the test substance-administered group as compared with the control group (the placebo-administered group or the non-administered group) or a reduction which is preferably statistically significant is recognized, the test substance can be identified to be a substance which reduces the amount of biophotons.

Then, the test substance which reduces the amount of biophotons identified can be evaluated to be a UV sensitivity-reducing agent.

The UV sensitivity-reducing agent thus selected can be used as a skin external preparation for reducing the UV sensitivity or can be used as a material or a formulation for reducing the UV sensitivity to be mixed with the skin external preparation, for example.

Relating to the aforementioned embodiments, the following embodiments are further disclosed in the present invention.

<1> A method for determining a UV sensitivity, comprising: a step of irradiating the skin of a test subject with ultraviolet light to determine the UV sensitivity using the amount of biophotons to be detected within a specific period after the irradiation, wherein 50% or more of the specific period overlaps a period from 1 to 3 minutes after the irradiation.

<2> The method according to <1>, wherein the specific period has a length of from 30 seconds to 3 minutes, more preferably from 40 seconds to 2 minutes, more preferably from 50 seconds to 1 minute and 30 seconds, more preferably 1 minute.

<3> The method according to <1> or <2>, wherein the specific period is 1 minute from 1 to 2 minutes after the UV irradiation, 1 minute from 2 to 3 minutes after the UV irradiation, or 2 minutes from 1 to 3 minutes after the UV irradiation.

<4> The method according to any of <1> to <3>, wherein the UV irradiation is irradiation with mixed ultraviolet light of A radiation and B radiation.

<5> The method according to any of <1> to <4>, wherein the UV irradiation is performed at a UV irradiation dose of from 300 to 8000 $mJ/cm^2$, more preferably from 500 to 7000 $mJ/cm^2$, further preferably from 600 to 6000 $mJ/cm^2$.

<6> The method according to any of <1> to <5>, wherein the amount of biophotons is calculated based on the luminescence intensity of biophotons.

<7> The method according to any of <1> to <6>, wherein the UV sensitivity is erythema formation by ultraviolet light.

<8> A method for evaluating or searching for a UV sensitivity-reducing agent, comprising: a step of administering a test substance to a subject or bringing the test substance into contact with the subject; and a step of irradiating the skin or skin cells of the subject with ultraviolet light to evaluate the test substance using the amount of biophotons to be detected within a specific period after the irradiation, wherein 50% or more of the specific period overlaps a period from 1 to 3 minutes after the irradiation.

<9> The method according to <8>, wherein the subject is a human, cultured epidermal cells, a 3D skin model, or a cultured skin tissue.

<10> The method according to <8> or <9>, wherein the administration of the test substance to the subject or the contact of the test substance with the subject is performed at a specific frequency of once or multiple times within a specific administration or contact period provided before the UV irradiation.

<11> The method according to <10>, wherein the administration of the test substance to the subject is performed during an administration period of preferably one day or more, more preferably one week or more, more preferably 4 weeks or more, and preferably 6 months or less, more preferably 3 months or less, more preferably 2 months or less, at an administration frequency of preferably once or more, more preferably once to 5 times, more preferably once to 3 times, more preferably twice, per day.

<12> The method according to <10>, wherein the contact of the test substance with the cultured epidermal cells, the 3D skin model, or the cultured skin tissue is performed for a contact period of preferably 1 hour or more, more preferably 6 hours or more, more preferably 24 hours or more, and preferably 72 hours or less, more preferably 36 hours or less, more preferably 48 hours or less, at a contact frequency of preferably once or more, more preferably once to 4 times, more preferably once or twice, during the contact period.

EXAMPLES

UV Irradiation Device

A 300-W xenon light source (MAX-301, available from Asahi Spectra Co., Ltd.) including a xenon lamp to which a WG-320 filter (with a thickness of 1 mm, available from Shibuya Optical Co., Ltd.) had been attached was used as a light source (ultraviolet A radiation (UVA): ultraviolet B radiation (UVB)=10.8:1).

Test Example 1

Weak Luminescence by UV Irradiation in Human

The test subject was a healthy male in his 30s and was subjected to measurement after habituation in a dark room for 10 minutes. For the measurement, a weak luminescence intensity detector (CLA-IDFsk, available from Tohoku Electronic Industrial CO., Ltd.) was used, and the attachment of the detection unit of the device was brought into close contact with an inner forearm in the sitting position. Fibers for light irradiation extending from the UV irradiation device were connected to be integrated with the attachment of the detection unit, so as to form a structure capable of switching between UV irradiation and weak luminescence intensity detection by changing the optical path. Various sites were irradiated with ultraviolet light (respectively, with a UV intensity of 15.4, 32.5, or 61.6 mW/cm$^2$, an irradiation time of 120 seconds, and a UV irradiation dose of 1.8, 3.9, or 7.4 J/cm$^2$), and the luminescence intensity 2 seconds after the completion of the irradiation was measured for 10 minutes for each site.

FIG. 1 shows the measurement results. It was confirmed that the amount of biophotons by the UV irradiation from the skin reached a maximum immediately after the UV irradiation, then rapidly decreased, and gradually decreased with time after a certain amount of decrease.

Test Example 2

Measurement of Weak Luminescence and Evaluation of Erythema in Human (1)

The UV irradiation and detection of weak luminescence intensity were performed by the same procedure using the same device as in Test Example 1. The test subject was 3 healthy males in their 20s to 30s, and the attachment of the detection unit of the device was brought into close contact with an inner forearm in the sitting position. The luminescence intensity when stable was measured for 3 minutes before the UV irradiation. Subsequently, UV irradiation was performed, and the luminescence intensity 2 seconds after the completion of the irradiation was measured for 10 minutes. A value obtained by subtracting the luminescence when stable from an average luminescence during each time period was calculated as a luminescence increment by the UV irradiation. The UV irradiation and subsequent measurement of weak luminescence were performed under multiple UV irradiation conditions with the irradiation site varied. Table 1 shows specific irradiation conditions and the measurement results.

Further, erythema formation in each UV-irradiated site was evaluated as the redness difference (Δa*) between the irradiation site and the non-irradiation site in the vicinity of the irradiation site by measuring the skin color 24 hours after the irradiation using a high-speed spectrophotometer (CMS-35FS, available from MURAKAMI COLOR RESEARCH LABORATORY). Table 1 shows the results.

From the results in Table 1, the correlation coefficient (R) between Δa* and the luminescence increment by the UV irradiation was calculated (Table 2).

TABLE 1

|  |  | Subject #1 | | | | Subject #2 | | |
| --- | --- | --- | --- | --- | --- | --- | --- | --- |
| Irradiation dose (mW/cm$^2$) | | 50 | 50 | 100 | 100 | 60 | 60 | 60 |
| Irradiation time (sec) | | 15 | 30 | 5 | 15 | 5 | 15 | 30 |
| Irradiation energy (mJ/cm$^2$) | | 750 | 1500 | 500 | 1500 | 300 | 900 | 1800 |
| Luminescence increment | Ave 2-10 s | 4541.7 | 4518.7 | 4824.0 | 5717.4 | 3311.1 | 3016.9 | 4494.8 |
| | Ave 11-60 s | 309.3 | 347.2 | 274.5 | 334.9 | 278.3 | 267.2 | 346.3 |
| | Ave 1-2 min | 61.3 | 80.9 | 49.5 | 77.1 | 53.3 | 55.0 | 70.3 |
| | Ave 2-3 min | 31.3 | 31.5 | 17.5 | 34.6 | 17.7 | 23.7 | 27.6 |
| | Ave 3-4 min | 20.4 | 22.4 | 14.8 | 17.2 | 17.9 | 14.7 | 20.9 |
| | Ave 4-5 min | 7.0 | 19.6 | 7.4 | 14.6 | 9.2 | 4.6 | 10.3 |
| Δa* | | 0.89 | 1.76 | −0.19 | 3.83 | 0.30 | 1.12 | 3.27 |

|  |  | Subject #2 | | | | Subject #3 | | |
| --- | --- | --- | --- | --- | --- | --- | --- | --- |
| Irradiation dose (mW/cm$^2$) | | 120 | 120 | 60 | 60 | 60 | 120 | 100 |
| Irradiation time (sec) | | 5 | 15 | 5 | 15 | 30 | 15 | 5 |
| Irradiation energy (mJ/cm$^2$) | | 600 | 1800 | 300 | 900 | 1800 | 1800 | 500 |
| Luminescence increment | Ave 2-10 s | 6613.8 | 5259.6 | 3285.8 | 3189.9 | 3568.1 | 5064.9 | 5258.8 |
| | Ave 11-60 s | 333.9 | 288.4 | 216.7 | 257.4 | 294.0 | 291.2 | 213.8 |
| | Ave 1-2 min | 54.8 | 54.9 | 38.1 | 53.5 | 70.7 | 56.9 | 35.0 |
| | Ave 2-3 min | 25.7 | 25.4 | 18.4 | 19.0 | 26.9 | 31.7 | 16.2 |
| | Ave 3-4 min | 16.7 | 16.4 | 10.9 | 16.2 | 22.9 | 15.8 | 4.0 |
| | Ave 4-5 min | 12.5 | 8.4 | 4.5 | 16.2 | 16.0 | 12.7 | 3.0 |
| Δa* | | 1.19 | 1.91 | 0.21 | 0.07 | 5.30 | 4.74 | 1.10 |

TABLE 2

Correlation coefficient between average luminescence increment and Δa* in each time period

| Time period | Correlation coefficient |
|---|---|
| 2-10 seconds | 0.218 |
| 11-60 seconds | 0.439 |
| 1-2 minutes | 0.580* |
| 2-3 minutes | 0.680** |
| 3-4 minutes | 0.403 |
| 4-5 minutes | 0.450 |

*$p < 0.05$,
**$p < 0.01$

Test Example 3

Measurement of Weak Luminescence and Evaluation of Erythema in Human (2)

The UV irradiation and detection of weak luminescence intensity were performed by the same procedure using the same device as in Test Example 1. The test subject was 10 healthy males in their 20s to 30s, and the attachment of the detection unit of the device was brought into close contact with an upper inner arm in the sitting position. The luminescence intensity when stable was measured for 3 minutes before the UV irradiation. Subsequently, UV irradiation was performed, and the luminescence intensity 2 seconds after the completion of the irradiation was measured for 5 minutes. A value obtained by subtracting the luminescence when stable from an average luminescence during each time period was calculated as a luminescence increment by the UV irradiation. The UV irradiation and subsequent measurement of weak luminescence were performed under multiple UV irradiation conditions with the irradiation site varied. Table 3 shows specific irradiation conditions and the measurement results.

Further, erythema formation in the UV-irradiated site was evaluated as the redness difference (Δa*) in the same manner as in Test Example 2, and Table 3 shows the results.

From the results in Table 3, the correlation coefficient (R) between Δa and the luminescence increment by the UV irradiation was calculated (Table 4).

TABLE 3

| | Irradiation dose (mW/cm$^2$) | Irradiation time (sec) | Irradiation energy (mJ/cm$^2$) | Luminescence increment Ave 0-1 min | Ave 1-2 min | Ave 2-3 min | Ave 3-4 min | Ave 4-5 min | Δa* |
|---|---|---|---|---|---|---|---|---|---|
| Sub #1 | 37.5 | 30 | 1125 | 1482.4 | 75.8 | 39.5 | 21.0 | 21.3 | −0.15 |
| | 75 | 15 | 1125 | 1945.7 | 68.5 | 31.2 | 18.2 | 12.7 | 0.24 |
| | 75 | 30 | 2250 | 2319.3 | 75.2 | 34.6 | 21.4 | 12.5 | 4.69 |
| | 112.5 | 30 | 3375 | 3861.3 | 120.7 | 53.3 | 32.6 | 26.9 | 6.46 |
| Sub #2 | 37.5 | 30 | 1125 | 2049.7 | 84.8 | 41.9 | 17.4 | 9.0 | 0.56 |
| | 75 | 15 | 1125 | 2505.3 | 81.0 | 39.8 | 21.0 | 14.4 | 1.00 |
| | 75 | 30 | 2250 | 2497.8 | 102.8 | 51.2 | 30.7 | 19.4 | 1.49 |
| | 112.5 | 30 | 3375 | 3503.4 | 110.0 | 51.9 | 34.9 | 21.4 | 4.81 |
| Sub #3 | 37.5 | 30 | 1125 | 2165.4 | 77.2 | 31.3 | 17.3 | 11.6 | −0.19 |
| | 75 | 15 | 1125 | 2969.4 | 66.8 | 31.1 | 17.9 | 3.4 | 0.03 |
| | 75 | 30 | 2250 | 3887.9 | 72.3 | 33.7 | 19.2 | 13.0 | 1.40 |
| | 112.5 | 30 | 3375 | 4211.1 | 99.8 | 46.9 | 27.8 | 13.6 | 1.97 |
| Sub #4 | 37.5 | 30 | 1125 | 2223.0 | 66.2 | 28.9 | 18.5 | 17.0 | 0.80 |
| | 75 | 15 | 1125 | 2918.4 | 79.9 | 35.0 | 22.7 | 12.7 | 0.98 |
| | 75 | 30 | 2250 | 2786.7 | 84.4 | 41.8 | 29.9 | 15.1 | 1.17 |
| | 112.5 | 30 | 3375 | 4305.2 | 110.8 | 48.2 | 26.8 | 19.5 | 7.03 |
| Sub *5 | 37.5 | 30 | 1125 | 2205.0 | 88.1 | 36.9 | 21.0 | 18.1 | 1.30 |
| | 75 | 15 | 1125 | 3174.3 | 84.3 | 36.1 | 19.9 | 9.7 | 0.66 |
| | 75 | 30 | 2250 | 3326.0 | 89.7 | 35.2 | 20.1 | 11.0 | 2.76 |
| | 112.5 | 30 | 3375 | 4397.1 | 96.8 | 43.3 | 19.7 | 13.4 | 6.72 |
| Sub #6 | 37.5 | 30 | 1125 | 2519.7 | 85.6 | 33.7 | 23.8 | 15.4 | 0.10 |
| | 75 | 15 | 1125 | 3721.4 | 80.8 | 36.6 | 13.1 | 17.5 | 0.49 |
| | 75 | 30 | 2250 | 3511.1 | 92.7 | 46.6 | 30.8 | 20.7 | 0.47 |
| | 112.5 | 30 | 3375 | 3736.2 | 90.0 | 36.8 | 23.1 | 15.0 | 2.21 |
| Sub #7 | 37.5 | 30 | 1125 | 1816.0 | 67.7 | 23.6 | 15.9 | 6.4 | 0.44 |
| | 75 | 15 | 1125 | 2399.4 | 73.1 | 31.2 | 17.1 | 10.1 | 1.13 |
| | 75 | 30 | 2250 | 2640.3 | 78.8 | 35.2 | 21.7 | 15.2 | 1.48 |
| | 112.5 | 30 | 3375 | 3659.8 | 112.2 | 50.6 | 23.7 | 17.7 | 4.98 |
| Sub #8 | 37.5 | 30 | 1125 | 2001.2 | 74.9 | 35.3 | 22.6 | 13.1 | −0.32 |
| | 75 | 15 | 1125 | 2751.7 | 70.2 | 34.7 | 21.3 | 16.8 | 0.35 |
| | 75 | 30 | 2250 | 2887.8 | 95.0 | 43.4 | 25.9 | 21.7 | 2.39 |
| | 112.5 | 30 | 3375 | 3600.1 | 85.2 | 39.1 | 26.8 | 13.1 | 8.34 |
| Sub #9 | 37.5 | 30 | 1125 | 2173.3 | 67.3 | 27.5 | 15.1 | 6.3 | 0.50 |
| | 75 | 15 | 1125 | 4074.8 | 84.4 | 34.9 | 20.0 | 12.3 | 0.21 |
| | 75 | 30 | 2250 | 3078.4 | 86.4 | 36.3 | 16.2 | 6.7 | 1.82 |
| | 112.5 | 30 | 3375 | 4441.5 | 99.3 | 53.1 | 33.3 | 15.5 | 5.55 |
| Sub #10 | 37.5 | 30 | 1125 | 4630.7 | 103.1 | 44.8 | 22.8 | 15.9 | 0.12 |
| | 75 | 15 | 1125 | 4034.8 | 95.3 | 43.7 | 26.9 | 12.7 | −0.11 |
| | 75 | 30 | 2250 | 3745.7 | 98.5 | 43.6 | 16.9 | 15.8 | 1.77 |
| | 112.5 | 30 | 3375 | 5303.1 | 109.4 | 47.2 | 37.4 | 16.7 | 2.00 |

TABLE 4

Correlation coefficient between average luminescence increment and Δa* in each time period

| Time period | Correlation coefficient |
|---|---|
| 0-1 minutes | 0.449 |
| 1-2 minutes | 0.563** |
| 2-3 minutes | 0.525** |
| 3-4 minutes | 0.423 |
| 4-5 minutes | 0.326 |

**$p < 0.01$

As shown in Table 2 and Table 4, it is understood that the amount of biophotons (response biophotons) detected within the periods of from 1 to 2 minutes and from 2 to 3 minutes after the UV irradiation has a significant positive correlation with the degree of erythema formation after the UV irradiation.

Accordingly, the sensitivity related to inflammatory reactions typified by erythema formation by ultraviolet light can be determined using the amount of biophotons to be detected mainly within a period of from 1 to 3 minutes after the UV irradiation as an index.

Test Example 4

Evaluation of UV Sensitivity-Reducing Agent

1) Test Subject: 10 Healthy Adult Japanese Males
2) Test Item:
    3.0% (v/v) Pharcolex rosemary E aqueous solution
    1.0% (v/v) Pharcolex rosemary E aqueous solution
    Placebo aqueous solution
    The symbol * represents the concentration of Pharcolex rosemary E (available from ICHIMARU PHARCOS Co., Ltd.) in each aqueous solution that behaves as a test item.
3) Measurement and Analysis of Response Biophotons:
    The response biophotons were calculated by measuring stationary biophotons and biophotons after the irradiation shown below and subtracting the measured value of the stationary biophotons from the measured value of the biophotons after the irradiation during the period of from 1 to 3 minutes after the completion of the photoirradiation. A significance test was conducted as statistical analysis by one-way analysis of variance and Bonferroni's multiple comparison.
    <Stationary Biophotons>
    The weak luminescence at each test site before the UV irradiation was measured for 1 minute using a weak luminescence intensity detector (CLA-IDFsk, available from Tohoku Electronic Industrial CO., Ltd).
    <Biophotons after Irradiation>
    The test site was irradiated with 1430-mJ/cm$^2$ ultraviolet light (the same wavelength range as sunlight) using the same UV irradiation device as in Test Example 1, and the weak luminescence of each test site from immediately after the UV irradiation to 3 minutes after the UV irradiation was measured using the weak luminescence intensity detector.
4) Test Procedure:
    The abdomen was cleaned with a wet tissue, and 3 points were marked as test sites. Each test site was set in a 5-cm square (5×5 cm). After habituation in a dark room for 10 minutes, biophotons were measured. Each test item was applied to each of the 3 test sites at 2 mg/cm$^2$ twice per day (morning and evening) for 4 weeks from the evening of the measurement date. After continuous use, biophotons were measured by the same procedure as before continuous use.

Figure 2:
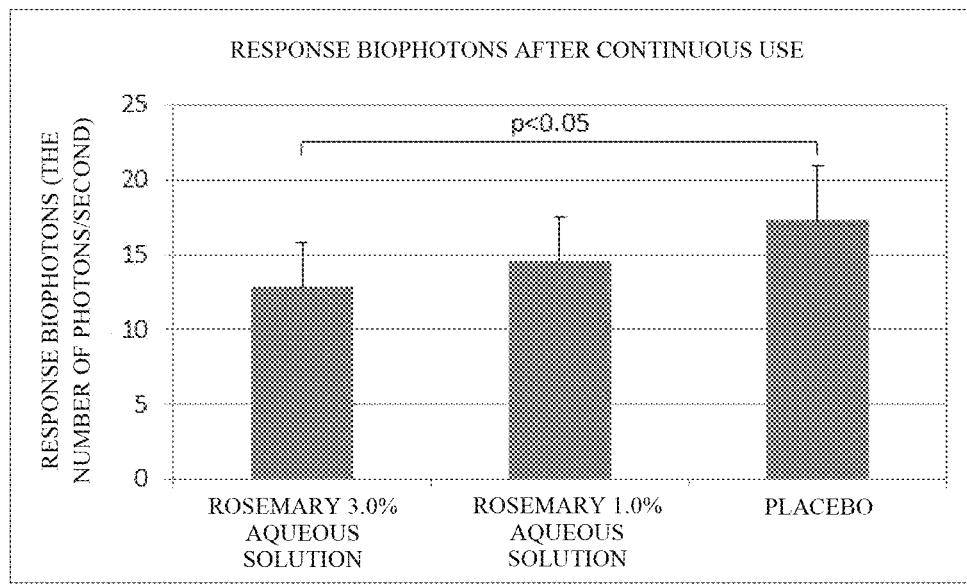
FIG. 2 is a graph showing the amount of response biophotons after continuous application of a rosemary aqueous solution.

5) Results
    FIG. 2 shows the values of response biophotons after continuous use. As a result of comparison with placebo, a significant reduction was observed in the rosemary 3.0% aqueous solution. It is known that preliminary application of an extract of rosemary suppresses erythema formation by UV irradiation (JP-A-2002-87975).

Test Example 5

Evaluation of UV Sensitivity-Reducing Agent
(Evaluation Using Cultured Cells)

1) Cells: Epidermal Keratinocytes Derived from Normal Human Neonatal Foreskin (Frozen HEKn, LifeTechnologies) (Culture Conditions)
    The cells were cultured in a growth medium for epidermal keratinocytes (EpiLife, LifeTechnologies) containing a growth additive (HuMedia-KG, available from KURABO INDUSTRIES LTD.) under conditions of 37° C. and 5% $CO_2$ according to a conventional method. A cell suspension obtained by suspending cells which were washed with Hank's Balanced Salt Solutions (HBSS, Invitrogen) and then collected, in HBSS at 4×10$^6$ cells/ml was subjected to the measurement of the weak luminescence.
2) Test Item: Trolox (6-hydroxy-2,5,7,8-Tetramethylchroman-2-Carboxylic Acid) (Aldrich)
3) Measurement of Response Biophotons:
    The response biophotons were calculated by measuring stationary biophotons and biophotons after the irradiation shown below and subtracting the measured value of the stationary biophotons from the measured value of the biophotons after the irradiation during the period of from 2 to 3 minutes after the completion of the photoirradiation. The biophoton measurement and the UV irradiation were performed under conditions with the cover of a dish detached.
    <Stationary Biophotons>
    1.0 ml of the cell suspension was taken into a 35-mm dish, and the luminescence intensity before the UV irradiation was measured in a dark room for 3 minutes using a weak luminescence intensity detector (CLA-IDFsk, available from Tohoku Electronic Industrial CO., Ltd).
    <Biophotons After the Irradiation>
    Using the same UV irradiation device as in Test Example 1, irradiation with a solar UV simulator light (125 mW/cm$^2$) was performed for 40 seconds, and the luminescence intensity after the irradiation was measured for 5 minutes.
4) Test Method
    Trolox (final concentration of 100 μM) or a control solvent (70% ethanol) was added to normal human epidermal keratinocytes in a 70 to 80% confluent state. 24 hours later, the cells were collected, and response biophotons were measured based on the aforementioned method. The measurement data was relatively evaluated with the value of the control solvent group taken as 1.
5) Results
    As shown in Table 5, a tendency to suppress the intensity of response biophotons was recognized in the group supplemented with Trolox, which is known as a water-soluble analog of vitamin E and as an antioxidant, as compared with the control solvent group (p<0.1: t test with no correspondence, both sides).

TABLE 5

|  | Control solvent | Trolox-supplemented |
|---|---|---|
| Intensity of response biophotons (average ± standard deviation) | 1.000 ± 0.216 | 0.722 ± 0.170† |

(†p < 0.1)

Test Example 6

Evaluation of UV Sensitivity-Reducing Agent
(Evaluation Using Tissue Culture Skin)

1) Skin tissue: Normal human skin tissue derived from surgery was purchased from American skin bank, National Disease Research Interchange (NDRI). A consent for use of the skin tissue for research applications has been made in a written document by a tissue provider.
(Culture Conditions)

After trimming the subcutaneous fat, the human skin tissue was cut with a knife into small pieces having a size of about 1 cm×1 cm and was cultured under conditions of 37° C. and 5% $CO_2$ using a 6-well plate. Advanced Dulbecco's Modified Eagle Medium containing 10% (v/v) Fetal Bovine Serum (FBS) (both available from Life Technologies) was used for the culture.

The skin one day after the culture was subjected to the biophoton measurement.

2) Test item: Trolox (6-hydroxy-2,5,7,8-tetramethylchroman-2-carboxylic acid)

3) Measurement of response biophotons:

Response biophotons were calculated by measuring stationary biophotons and biophotons after the irradiation shown below and subtracting the measured value of the stationary biophotons from the measured value of the biophotons after the irradiation during the period of from 1 to 3 minutes after the completion of the photoirradiation. The biophoton measurement and the UV irradiation were performed under conditions in which the skin tissue had been taken out of the culture solution.
<Stationary Biophotons>

The luminescence intensity before the irradiation with solar UV simulator light was measured in a dark room for 3 minutes using a weak luminescence intensity detector (CLA-IDFsk, available from Tohoku Electronic Industrial CO., Ltd).
<Biophotons after Irradiation>

Using the same UV irradiation device as in Test Example 1, irradiation with a solar UV simulator light (30 $mW/cm^2$) was performed for 3 minutes and 20 seconds, and the luminescence intensity after the irradiation was measured for 5 minutes.

4) Test method

Trolox (final concentration of 100 μM) or the control solvent (70% ethanol) was added to the culture medium including the cultured human skin tissue one day after the culture. 24 hours later, the skin tissue was washed with PBS and then subjected to the measurement of response biophotons based on the aforementioned method. The measurement data was relatively evaluated with the value of the control solvent group taken as 1.

5) Results

As shown in Table 6, a significant suppression of the intensity of the response biophotons was recognized in the group supplemented with Trolox as compared with the control solvent group (p<0.05: t test with no correspondence, both sides).

TABLE 6

|  | Control solvent | Trolox-supplemented |
|---|---|---|
| Intensity of response biophotons (average ± standard deviation) | 1.000 ± 0.182 | 0.634 ± 0.143 * |

(* p < 0.05)

The invention claimed is:

1. A method for determining a UV sensitivity of skin to erythema formation in a test subject, the method comprising:
   irradiating a skin of a test subject with ultraviolet light, measuring the amount of biophotons produced by the skin after the irradiation, and determining the UV sensitivity of the skin to erythema formation using the amount of biophotons measured during a specified period after the irradiation, wherein the specified period is within a period of from 1 to 3 minutes after the irradiation.

2. The method according to claim 1, wherein the specific period has a length of from 30 seconds to 2 minutes.

3. The method according to claim 1, wherein the specific period is 1 minute from 1 to 2 minutes after the UV irradiation, 1 minute from 2 to 3 minutes after the UV irradiation, or 2 minutes from 1 to 3 minutes after the UV irradiation.

4. The method according to claim 1, wherein the UV irradiation is irradiation with mixed ultraviolet light of A radiation and B radiation.

5. The method according to claim 1, wherein the UV irradiation is performed at a UV irradiation dose of from 300 to 8000 $mJ/cm^2$.

6. The method according to claim 1, wherein the amount of biophotons is calculated based on the luminescence intensity of biophotons.

7. The method according to claim 1, wherein the specific period has a length of from 50 seconds to 1 minute and 30 seconds.

8. A method for evaluating or searching for a UV erythema formation sensitivity-reducing agent, the method comprising:
   administering a test substance to a subject or contacting the test substance with skin of the subject; and
   irradiating the skin or skin cells of the subject with ultraviolet light, measuring the amount of biophotons produced by the skin after irradiation, comparing the amount of biophotons produced during a specified period to a control based biophotons produced during the specified period after irradiation of the skin or skin cells, and determining that the test substance is a UV erythema formation sensitivity-reducing agent when the amount of biophotons after the administering or contacting the test substance is lower than the amount of biophotons produced from the control, wherein the specified period is within a period of from 1 to 3 minutes after the irradiation ultraviolet light and the amount of biophotons within said specific period after the irradiation.

9. The method according to claim 8, wherein the subject is a human, cultured epidermal cells, a 3D skin model, or a cultured skin tissue.

10. The method according to claim 9, wherein the contacting the test substance with the cultured epidermal cells, the 3D skin model, or the cultured skin tissue is performed for a contact period of from 1 hour to 72 hours, at a contact frequency of at least once during the contact period.

11. The method according to claim 8, wherein the administering the test substance to the subject or the contacting the test substance with the subject is performed at a specific frequency of at least once within a specific administration or contact period provided before the UV irradiation.

12. The method according to claim 8, wherein the administering the test substance to the subject is performed during an administration period of from one day to 6 months, at an administration frequency of at least once per day.

13. The method according to claim 8, wherein the amounts of biophotons are compared between a higher-concentration test substance-administered group and a lower-concentration test substance-administered group; between a test substance-administered group and a placebo-administered group; between a test substance-administered group and a non-administered group; or between before and after administration of each test substance.

* * * * *

UNITED STATES PATENT AND TRADEMARK OFFICE
CERTIFICATE OF CORRECTION

PATENT NO. : 11,486,830 B2
APPLICATION NO. : 16/958354
DATED : November 1, 2022
INVENTOR(S) : Yu Gabe et al.

Page 1 of 1

It is certified that error appears in the above-identified patent and that said Letters Patent is hereby corrected as shown below:

In the Claims

Claim 8, Column 16, Lines 65-67, delete "ultraviolet light and the amount of biophotons within said specific period after the irradiation".

Signed and Sealed this
First Day of July, 2025

Coke Morgan Stewart
*Acting Director of the United States Patent and Trademark Office*